United States Patent [19]

Tanaka et al.

[11] Patent Number: 4,758,643

[45] Date of Patent: Jul. 19, 1988

[54] DENTAL ADHESIVE RESIN COMPOSITIONS

[75] Inventors: Hisatoshi Tanaka; Kazuo Iwamoto, both of Morioka; Masayuki Takahashi, Tokyo; Akiyoshi Kotaka, Yoshikawa, all of Japan

[73] Assignee: G-C Dental Industrial Corp., Tokyo, Japan

[21] Appl. No.: 860,028

[22] Filed: May 6, 1986

[30] Foreign Application Priority Data

May 24, 1985 [JP] Japan ................. 60-110168

[51] Int. Cl.$^4$ .............................. C08F 30/08
[52] U.S. Cl. ...................... 526/279; 526/318.4
[58] Field of Search ................ 526/279, 318.4

[56] References Cited

U.S. PATENT DOCUMENTS

| | | | |
|---|---|---|---|
| 2,420,911 | 5/1947 | Roedel et al. | 526/279 |
| 3,835,090 | 9/1974 | Gander et al. | 526/279 |
| 4,147,685 | 4/1979 | Smith et al. | 526/279 |
| 4,398,007 | 8/1983 | Kubota et al. | 526/279 |

FOREIGN PATENT DOCUMENTS 1146215 3/1969 United Kingdom .

*Primary Examiner*—Joseph L. Schofer
*Assistant Examiner*—Peter D. Mulcahy
*Attorney, Agent, or Firm*—Oblon, Fisher, Spivak, McClelland & Maier

[57] ABSTRACT

A dental adhesive resin compositions by copolymerization of unsaturated carboxylic acids with vinyl or allyl esters of unsaturated carboxylic acids in the coexistence of (meth)acrylate base monomers which produce firm adhesion with respect to dental Co-Cr and Ni-Cr base alloys, and are used as plate materials or adhesives, the (meth)acrylic resin materials can firmly be bonded to even metal plates for which any special retention form is not applied, and bridges in which porcelain teeth are used as pontics.

46 Claims, No Drawings

DENTAL ADHESIVE RESIN COMPOSITIONS

BACKGROUND OF THE INVENTION

Field of the Invention

The present invention relates to a dental adhesive resin composition for imparting firm adhesion to dental nonprecious alloys or dental porcelain materials, thereby enhancing the usefulness thereof, without giving damage to the excellent physical properties of a (meth)acrylic resin materials widely used in dentistry.

Dental alloys have higher thermal conductivity than (meth)acrylic resin materials, and do not only serve to mitigate a feeling of physical disorder upon putting-in of dentures in view of the sense of temperature or taste, but do also excel in mechanical strength, dimensional accuracy and water resistance, as compared with the (meth)acrylic resin materials. Taking such advantages, the dental alloys are used at metal-based dentures or bridges in combination with the (meth)acrylic resin materials, and are considered to be increasingly demanded with the arrival of aging society.

Co-Cr and Ni-Cr base alloys typical of the dental nonprecious alloys have a Young's modulus of about two-fold at a specific gravity of about ½, as compared with precious alloys such as gold alloys, gold/silver/palladium alloys and platinum plus gold alloys, and offer considerable advantages to patients, since they do not only excel in the resistance to discoloration, but are also low price. Thus, the amount of the Co—Cr and Ni—Cr base alloys used are increasing year by year.

Commercially available (meth)acrylic resin materials for the preparation of dentures have no chemical bonding force with respect to dental alloys. For that reason, it is required to carry out designs at the time of preparing dentures, taking various mechanical retention forms into consideration, thus making technicians' manipulation complicated. In addition, due to the absence of any chemical bond between the dental alloys and the resin materials, a gap occurs at the junction of the resin and the metal, i.e., the so-called finishing line. This poses a number of problems such as partial separation and breakage of the resin, contamination and discoloration of portions of the resin around that junction due to the accumulation of foodstuff residues and filth, occurrence of denture plaque and odor, etc.

If (meth)acrylic resin materials could chemically bonded to metals, then the aforesaid problems would be solved. In addition, new techniques and denture designs could be introduced in dentistry.

Some attempts have been made so as to achieve such bonding. For instance, according to one of the methods heretofore reported, the surface of a metal is etched with an inorganic acid, applied thereon with a bonding agent, and is further laminated thereon with an MMA base plate resin material. According to another method, 4-methacryloxyethyl trimellitic anhydride is incorporated into an MMA monomer. However, these methods make technicians' manipulation complicated, and give no bonding force with respect to porcelain or ceramic teeth. According to a further method, a silane compound is added to an MMA monomer to afford adhesion to porcelain teeth. However, it is expected that this method would give no bonding force to any metal.

There are still further reports regarding porcelain teeth wherein a silane compound and an unsaturated carboxylic acid are allowed to coexist in an MMA monomer, and adhesive compositions for giving adhesion to metals. However, any high and stable adhesion is not always obtained.

SUMMARY OF THE INVENTION

According to the present invention, it has been found that the products obtained by copolymerization of unsaturated carboxylic acids with vinyl or allyl esters of unsaturated carboxylic acids in the coexistance of (meth)acrylate base monomers produce firm adhesion with respect to dental Co—Cr and Ni—Cr base alloys. It has also been found that the products further containing a silane compound can be bonded to porcelain teeth (porcelain).

DETAILED DESCRIPTION OF THE PREFERRED EMBODIMENTS

When the dental adhesive resin compositions according to the present invention are used as plate materials or adhesives, the (meth)acrylic resin materials can firmly be bonded to even metal plates for which any special retention form is not applied, and bridges in which porcelain teeth are used as pontics. The thus prepared dentures excel in strength, suffer from reduced or limited contamination, and are easily manipulated by technicians.

Of these compositions, some compositions obtained by dissolving the unsaturated carboxylic acids alone in the (meth)acrylate-base monomers are of limited adhesion to metals and reduced durability. However, in spite of the fact that the vinyl or allyl esters of unsaturated carboxylic acids per se display no adhesion to metals, firm adhesion to metals is synergistically produced, if they are allowed to coexist with the unsaturated carboxylic acids dissolved in the (meth)acrylate base monomers. Besides, further addition of the silane compounds gives rise to more firm adhesion to the surface of porcelain teeth activated by the co-existence of the unsaturated carboxylic acids.

The compositions according to the present invention give such adhesion without impairing the advantages of the generally used dental (meth)acrylic resin materials have, such as, for instance, appearance, manipulation properties and adhesion to resin teeth as well as excellent physical/chemical properties such as mechanical strength, water resistance, etc.

Referring to shelf stability, the compositions of the present invention underwent no setting even after the lapse of as long as two years from the addition of 100 ppm hydroquinone.

In the following, the present invention will be described in further detail.

A liquid component is prepared by incorporating 0.5-10% by weight of unsaturated carboxylic acids and 0.5-20% by weight of vinyl or allyl esters of unsaturated carboxylic acids into (meth)acrylate base monomers. No higher than 400 parts by weight of a filler and 0.1-10 parts by weight of a setting agent are added to 100 parts by weight of the liquid component. As the filler use is made of a (meth)acrylic polymer powder, an inorganic fine powder such as silica, titanium oxide and alumina, or a finely divided composite material thereof. The resulting product is molded into denture in the manner ordinarily used in the dental field.

According to the compositions of the present invention, the unsaturated carboxylic acids and the vinyl or allyl esters of unsaturated carboxylic acids have an synergistic action upon the Co—Cr or Ni—Cr base alloys during polymerization, when preparing metal-plated dentures or bridges, thus resulting in firm bonding.

Further addition of silane compounds to the aforesaid compositions in an amount of 0.5–20 parts by weight gives firm adhesion to not only the aforesaid alloys but also porcelain teeth (materials).

The unsaturated carboxylic acids used in the present invention are expressed in terms of the following general formula:

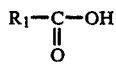

wherein R₁ is a polymerizable substituent having at least one double bond, and may preferably include, e.g., acrylic acid, methacrylic acid, crotonic acid, undecenoic acid, cinnamic acid, vinylacetic acid, pyroterebic acid, sorbic acid, hydrosorbic acid, teracrylic acid, geranic acid, oleic acid, erucic acid, linoleic acid and linolenic acid. Particular preference is given to acrylic acid, methacrylic acid and undecenoic acids.

In the present invention, it is understood that the unsaturated carboxylic acids may include, in addition to the aforesaid unsaturated monocarboxylic acids, unsaturated di- and tetra-carboxylic acids.

The vinyl or allyl esters of unsaturated carboxylic acids used in the present invention are expressed in terms of the following general formula:

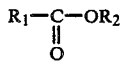

wherein R₁ is a polymerizable substituent having at least one double bond, and R₂ is a vinyl group (CH₂=CH—) or an allyl group (CH₂=CH—CH₂—), and may include vinyl acrylate, vinyl methacrylate, vinyl crotonate, vinyl undecenate, vinyl cinnamate, vinyl vinylacetate, vinyl pyroterebate vinyl sorbate, vinyl hydrosorbate, vinyl teracrylate, vinyl geranate, vinyl oleate, vinyl eruciate, vinyl linoleate, vinyl linolenate, etc. The corresponding allyl esters may also be used. Of these esters, the most preference is given to vinyl sorbate.

The monomers (C) used in the present invention may embrace those based on (meth)acrylates, for instance, methyl methacrylate, ethyl methacrylate, ethylene glycol dimethacrylate, diethylene glycol dimethacrylate, triethylene glycol dimethacrylate, tetraethylene glycol dimethacrylate, 1,4-butanediol dimethacrylate, neopentyl glycol dimethacrylate, trimethylolpropane trimethacrylate, pentaerythritol tetramethacrylate, 2,2-bis(4-methacryloxyphenyl)propane, 2,2-bis(4-methacryloxypolyethoxy)phenylpropane, 2,2-bis(4-(2-hydroxy-3-methacryloxypropoxy)phenyl)propane and 1,3-bis(methacryloxyethoxy)benzene.

Of these monomers, methyl methacrylate is preferable for use in the dental plate materials.

The fillers used in the present invention may include organic fillers such as, for instance, polymethyl methacrylate, copolymers of methyl methacylate and methacrylates, copolymers of methyl methacrylate and styrene and the like, and inorganic fillers such as borosilicate glass, quartz, feldspar, amorphous silica, alumina, alumina silicate, titanium oxide and the like. The organic and inorganic fillers may be used alone or in combination. Alternatively, use may be made of the so-called composite filler in which the inorganic filler is coated with an organic polymer.

The silane compound used to give adhesion to porcelain teeth are expressed in terms of the following general formula:

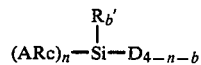

wherein
D is a hydrolyzable group,
n is an integer of 1–3,
b is 0, 1 or 2,
n+b is an integer of 1–3,
R' is a group selected from the group consisting of monovalent hydrocarbons,
R is an alkylene group having C₁₋₄ carbon atoms,
c is 0 or 1, and

A: —CH=CH₂,

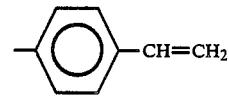

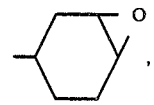

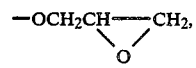

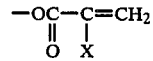

wherein X is a hydrogen atom or a hydrocarbon group having C₁₋₆ carbon atoms.

In the foregoing formula, D may be any group that is hydrolyzable. In the silane compounds, the number of D may be one, two or three, preferably three.

Typical D may be methoxy, ethoxy, propoxy, isopropoxy and the like group.

R' may be any monovalent hydrocarbon group, and is, for instance, methyl, ethyl, propyl, butyl, etc. Recommendable is methyl group. b may be 1, 2 or 0.

The number of the ARc groups may 1, 2 or 3. In other words, n may be 1, 2 or 3. Preferably, n is 1. The R group is bonded to a silicon atom, and is a divalent alkylene group having 1 to 4 carbon atoms. For instance, R stands for methylene, ethylene, trimethylene, propylene and the like groups. c may be 0 or 1. Any R may not be allowed to be present. A is bonded to the R group, except that c is 0, and is bonded directly to a silicon atom.

A is any one group of

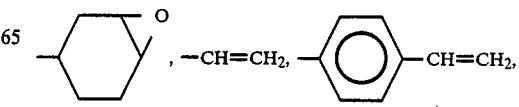

-continued

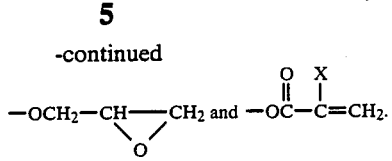

When C is 0, A is

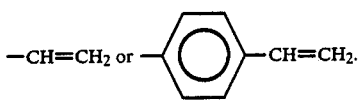

In

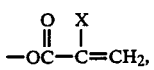

x stands for a hydrocarbon group having 1 to 6 carbon atoms. In this case, an ester group is present in the compound. For instance, X stands for methyl, ethyl, ispropyl, butyl or the like group.

Typical examples of the compounds according to the foregoing definition are commercially available, and include γ-glycidoxypropyltrimethoxysilane, γ-glycidoxyopropyltriethoxysilane, γ-methacryloxypropyltrimethoxysilane, γ-methacryloxypropyltriethoxysilane, vinyltriethoxysilane, β-(3,4-epoxycyclohexyl)ethyltrimethoxysilane, vinyl.tris(β-methoxyethoxy)silane, etc.

The setting agents to be used in the present invention include oxidizing agents such as organic peroxides represented as by benzoyl peroxide, lauryl peroxide, cumene hydroperoxide, etc., and azo compounds such as 2,2-azobisisobutylonitrile, etc. Among these compounds, preferable is benzoyl peroxide. In use, the oxidizing agents may be combined with reducing agents as represented by, e.g., tertiary amines such as dimethyl paratoluidine, 2-hydroxyethyl-p-toluidine, etc., or their salts, and organic sulfinates such as sodium p-benzenesulfinate, sodium p-toluenesulfinate, etc.

The concentrations of the aforesaid additives should be determined, taking into account various properties demanded for resin materials for denture plates, when dissolved in methyl methacrylate (MMA), and the adhesion to the Co—Cr and Ni—Cr base alloys and porcelain teeth.

Referring to the concentrations of the additives to be added into the MMA monomer, a bonding strength to the Co—Cr and Ni—Cr base alloys decreases to no higher than 40 kg/cm², when the amount of the unsaturated carboxylic acid is 0.5% by weight or less. In an amount exceeding 10% by weight, the resistance to transverse test drops to no higher than 5 kg that is unpractical.

When the amount of the vinyl or allyl ester of the unsaturated carboxylic acid is 0.5% by weight or lower, a bonding strength to the Ni—Cr base alloy drops to 40 kg/cm² or lower. This means that it fails to produce any synergistic effect with the unsaturated carboxylic acid. In an amount exceeding 20% by weight, the amount of deflection under a load of 5 kg in the transverse test exceeds 6 mm that does not meet the specification of JIS T6501, and is thus unpractical.

If 0.5 parts by weight or lower of the silane compound are added to 100 parts by weight of the MMA monomer containing the unsaturated carboxylic acid and the vinyl or ally ester of unsaturated carboxylic acid within the aforesaid concentration range, then the resulting bonding strength to porcelain teeth drops to 10 kg/cm² or lower. On the other hand, the addition of that silane compound in an amount exceeding 20 parts by weight causes the amount of deflection in the transverse test to exceed 6 mm that does not meet the specification of JIS T6501, and is thus unpractical.

From these results, the concentrations of the unsaturated carboxylic acids and the vinyl or allyl esters of unsaturated carboxylic acids are respectively determined as being 0.5–10% by weight and 0.5–20% by weight in the (meth)acrylate monomer. The amount of the silane compound to be added to 100 parts by weight of that composition is also determined as being 0.5–20 parts by weight.

The examples of the present invention were carried out under the following conditions. The results are all set forth in the table to be given later.

EXAMPLES 1–5 AND COMPARISON EXAMPLES 1–5

Condition I

Powdery polymethyl methacrylate (hereinafter abbreviated as MMA and having a particle size of 120–150 Tyler mesh) containing 0.1% benzoyl peroxide (hereinafter abbreviated as BPO) was used as the filler component. Kneading was carried out at the following powder/liquid ratio (by weight) of 2/1 to form a dough, which was pre-polymerized at 70° C. for 30 minutes and was in turn polymerized by heating at 100° C. to measure the tensile bond strength with respect to the Co—Cr and Ni—Cr base alloys and the porcelain materials.

EXAMPLES 6–7 AND COMPARISON EXAMPLES 6–7

Condition II

Powdery PMMA (having a particle size of 120–150 Tyler mesh) containing 1% BPO and 0.5% sodium p-toluenesulfinate was used as the filler component. The liquid component contained as the tertiary amine dimethyl p-toluidine. Kneading was carried out at the following powder/liquid ratio (by weight)=2/1 to form a dough, which was in turn polymerized and cured at room temperature to measure the tensile bond strength with respect to the Co—Cr and Ni—Cr base alloys and the porcelain materials.

The bonding test with respect to the metal and porcelain materials were in the following manner. Each metal test piece of 10×10×2 mm had its application surface finish-polished with emery paper (No. 1500).

Condition I

Wax was risen at the middle of the test piece in the cylindrical form of φ6×6 mm. The resultant product was embeded into gypsum according to the ordinary dental manner, which was then set. Thereafter, the wax was removed from the product, which was in trun washed to obtain a negative mold. The resin dough was filled under pressure in that mold, and polymerized therein for testing.

Condition II

A resin dough was filled in a cylindrical silicone rubber mold, and was polymerized at room temperatures for testing.

EXAMPLES 8-9 AND COMPARISON EXAMPLES 8-9

Masking tapes of 6 mm in diameter were applied to the middle portions of polished test pieces (No. 1500 finished) of dental Co—Cr, Ni—Cr base alloys and porcelain material. A mixture of equal amounts of a liquid component (a) containing 1% BPO and (b) a liquid component containing 1% dimethyl p-toluidine as the tertiary amine was applied on the application surface of such pieces. The testing pieces were butted end-to-end, and were polymerized at room temperature for testing.

However, it is to be understood that the present invention is not limited to the figures mentioned in the following examples.

EXAMPLE 1

A liquid composition consisting of:

| MMA | 92 parts |
|---|---|
| Acrylic Acid | 3 parts |
| Undecenoic Acid | 2 parts |
| Sorbic Acid Vinyl Ester | 3 parts |

EXAMPLE 2

A liquid composition consisting of:

| MMA | 92 parts |
|---|---|
| Methacrylic Acid | 3 parts |
| Undecenoic Acid | 2 parts |
| Sorbic Acid Vinyl Ester | 3 parts |

EXAMPLE 3

A liquid composition consisting of:

| MMA | 92 parts |
|---|---|
| Acrylic Acid | 3 parts |
| Undecenoic Acid | 2 parts |
| Sorbic Acid Allyl Ester | 3 parts |

EXAMPLE 4

γ-glycidoxypropyltrimethoxysilane was added to the composition of Example 1 as the silane compound.

| MMA | 90 parts |
|---|---|
| Acrylic Acid | 3 parts |
| Undecenoic Acid | 2 parts |
| Sorbic Acid Vinyl Ester | 3 parts |
| γ - glycidoxypropylmethoxysilane | 2 parts |

EXAMPLE 5

A liquid composition consisting of:

| MMA | 90 parts |
|---|---|
| Acrylic Acid | 3 parts |
| Undecenoic Acid | 2 parts |
| Sorbic Acid Vinyl Ester | 3 parts |
| γ - methacryloxypropyltrimethoxysilane | 2 parts |

EXAMPLE 6

A liquid composition consisting of:

| MMA | 91 parts |
|---|---|
| Acrylic Acid | 3 parts |
| Undecenoic Acid | 2 parts |
| Sorbic Acid Vinyl Ester | 3 parts |
| Dimethyl p-toluidine | 1 part |

EXAMPLE 7

A liquid composition consisting of:

| MMA | 89 parts |
|---|---|
| Acrylic Acid | 3 parts |
| Undecenoic Acid | 2 parts |
| Sorbic Acid Vinyl Ester | 3 parts |
| γ - glycidoxypropyltrimethoxysilane | 2 parts |
| Dimethyl p-toluidine | 1 part |

EXAMPLE 8

Liquid compositions (a) and (b) consisting of:

| (a) 2,2-bis(4-(2-hydroxy-3-methacryloxy-propoxy)phenyl)propane (hereinafter abbreviated as Bis-GMA) | 50 parts |
|---|---|
| Triethylene Glycol Dimethacrylate | 50 parts |
| Acrylic Acid | 6 parts |
| Undecenoic Acid | 4 parts |
| Sorbic Acid Vinyl Ester | 6 parts |
| BPO | 1 part |
| (b) Bis-GMA | 50 parts |
| Triethylene Glycol Dimethacrylate | 50 parts |
| Dimethyl p-toluidine | 1 part |

EXAMPLE 9

Liquid compositions (a) and (b) consisting of:

| (a) Bis-GMA | 50 parts |
|---|---|
| Triethylene Glycol Dimethacrylate | 50 parts |
| Acrylic Acid | 6 parts |
| Undecenoic Acid | 4 parts |
| Sorbic Acid Vinyl Ester | 6 parts |
| γ - glycidoxypropyltrimethoxysilane | 4 parts |
| BPO | 1 part |
| (b) Bis-GMA | 50 parts |
| Triethylene Glycol Dimethacrylate | 50 parts |
| Dimethyl p-toluidine | 1 part |

COMPARISON EXAMPLE 1

Use was made of commercially available resin for dental plates.

COMPARISON EXAMPLE 2

A liquid composition consisting of:

| MMA | 97 parts |
|---|---|
| Acrylic Acid | 3 parts |

COMPARISON EXAMPLE 3

A liquid composition consisting of:

| MMA | 97 parts |

-continued

| | |
|---|---|
| Sorbic Acid Vinyl Ester | 3 parts |

COMPARISON EXAMPLE 4

A liquid composition consisting of:

| | |
|---|---|
| MMA | 98 parts |
| γ - glycidoxypropyltrimethoxysilane | 2 parts |

COMPARISON EXAMPLE 5

A liquid composition consisting of:

| | |
|---|---|
| MMA | 95 parts |
| Acrylic Acid | 3 parts |
| γ - glycidoxypropyltrimethoxysilane | 2 parts |

COMPARISON EXAMPLE 6

A liquid composition consisting of:

| | |
|---|---|
| MMA | 96 parts |
| Sorbic Acid Vinyl Ester | 3 parts |
| Dimethyl p-toluidine | 1 parts |

COMPARISON EXAMPLE 7

A liquid composition consisting of:

| | |
|---|---|
| MMA | 96 parts |
| Sorbic Acid Vinyl Ester | 3 parts |
| Dimethyl p-toluidine | 1 parts |

COMPARISON EXAMPLE 8

Liquid compositions (a) and (b) consisting of:

| | |
|---|---|
| (a) Bis-GMA | 50 parts |
| Triethylene Glycol Dimethacrylate | 50 parts |
| Acrylic Acid | 6 parts |
| BPO | 1 part |
| (b) Bis-GMA | 50 parts |
| Triethylene Glycol Dimethacrylate | 50 parts |
| Dimethyl p-toluidine | 1 part |

COMPARISON EXAMPLE 9

Liquid compositions (a) and (b) consisting of:

| | |
|---|---|
| (a) Bis-GMA | 50 parts |
| Triethylene Glycol Dimethacrylate | 50 parts |
| γ - glycidoxypropyltrimethoxysilane | 4 parts |
| BPO | 1 part |
| (b) Bis-GMA | 50 parts |
| Triethylene Glycol Dimethacrylate | 50 parts |
| Dimethyl p-toluidine | 1 part |

TENSILE BOND STRENGTH (kg/cm$^2$)

| | Example | | | Comparison Example | | |
|---|---|---|---|---|---|---|
| No. | Co—Cr | Ni—Cr | Porcelain material | Co—Cr | Ni—Cr | Porcelain material |
| 1 | 218 | 211 | 0 | 0 | 0 | 0 |
| 2 | 186 | 191 | 0 | 65 | 20 | 0 |
| 3 | 190 | 203 | 0 | 0 | 0 | 0 |
| 4 | 199 | 218 | 123 | 0 | 0 | 86 |
| 5 | 277 | 212 | 106 | 71 | 21 | 98 |
| 6 | 118 | 86 | 58 | 62 | 49 | 49 |
| 7 | 106 | 64 | 56 | 40 | 52 | 42 |
| 8 | 89 | 67 | 0 | 43 | 26 | 0 |
| 9 | 82 | 74 | 50 | 0 | 0 | 33 |

Crosshead speed 1 mm/min

EFFECT OF THE INVENTION (1) It is possible to obtain the resin compositions firmly bondable to dental Co—Cr and Ni—Cr base alloys by the copolymerization of unsaturated carboxylic acids, vinyl or allyl esters of unsaturated carboxylic acids and (meth)acrylate monomers.

(2) A silane compund is added to the composition of (1) for copolymerization, whereby it is possible to obtain the resin compositions firmly bondable to porcelain teeth (porcelain material) and dental Co—Cr and Ni—Cr base alloys.

The present invention relates to a resin composition firmly bondable to dental Co—Cr and Ni—Cr base alloys or porcelain teeth, and having the following various effects.

(1) When the composition of the present invention is used as the plate resin material for metal-plate dentures or partial plate dentures, the junction of the resin and the metal, i.e., the so-called finishing line, is firmly bonded together. Thus, any separation and breakage of the resin due to the occurrence of a gap are prevented. In addition, any contamination and discoloration of the resin and any occurrence of denture plaque and denture odor are also prevented.

(2) Since the composition of the present invention is bonded to a metal plate, the obtained mechanical strength is considerably improved as compared with that obtained when using adhesion-free resin.

(3) When the composition of the present invention is applied to the preparation of dentures using porcelain teeth, it is firmly bonded to the porcelain teeth. Thus, the resulting denture does not suffer any separation and contamination of the margin portion.

(4) When the composition of the present invention is used as the bonding agent for joining a metal to a porcelain tooth, it is possible to easily prepare a bridge wherein the porcelain tooth is used as the pontic.

(5) Since the composition of the present invention is firmly bonded to a metal, technicians' manipulation is more easily effected with no need of using any special mechanical retention form, at the time of designing metal portions.

What is claimed is:
1. A dental adhesive resin composition, comprising:
(i) 0.5 to 10% by weight of at least one unsaturated carboxylic acid (A) of the formula:

R$_1$—CO—OH where R$_1$ is a polymerizable hydrocarbon substituent having at least one double bond;

(ii) 0.5 to 20% by weight of at least one vinyl or allyl ester of an unsaturated carboxylic acid (B) of the formula:

$$R_1-CO-O-R_2$$

where $R_1$ is a polymerizable hydrocarbon substituent having at least one double bond and $R_2$ is $CH_2=CH-$ or $CH_2=CH-CH_2-$; and (iii) a monomer (C) copolymerizable with the said unsaturated carboxylic acid (A) and the said vinyl or allyl ester of an unsaturated carboxylic acid (B).

2. The composition of claim 1, wherein the said unsaturated carboxylic acid (A) is at least one member selected from the group consisting of acrylic acid, methacrylic acid, and undecenoic acid.

3. The composition of claim 1, wherein the said vinyl or allyl ester of an unsaturated carboxylic acid (B) is vinyl sorbate or allyl sorbate.

4. The composition of claim 2, wherein the said vinyl or allyl ester of an unsaturated carboxylic acid (B) is vinyl sorbate or allyl sorbate.

5. The composition of claim 1, wherein the said monomer (C) is a mono-functional (meth)acrylate-based monomer, a di-functional (meth)acrylate-based monomer, a tri-functional (meth)acrylate-based monomer, or a tetra-functional (meth)acrylate-based monomer.

6. A dental adhesive resin composition, comprising:
(i) 0.5 to 10% by weight of at least one unsaturated carboxylic acid (A) of the formula:

$$R_1-CO-OH$$

where $R_1$ is a polymerizable hydrocarbon substituent having at least one double bond;

(ii) 0.5 to 20% by weight of at least one vinyl or allyl ester of an unsaturated carboxylic acid (B) having the formula:

$$R_1-CO-O-R_2$$

where $R_1$ is a polymerizable hydrocarbon substituent having at least one double bond, and $R_2$ is $CH_2=CH-$ or $CH_2=CH-CH_2-$; and (iii) a monomer (C) copolymerizable with the said unsaturated carboxylic acid (A) and the said vinyl or allyl ester of an unsaturated carboxylic acid (B);

(iv) said composition containing from 0.1 to 10 parts by weight of a setting agent per 100 parts by weight of the said composition containing the said unsaturated carboxylic acid (A), the said vinyl or allyl ester of an unsaturated carboxylic acid (B) and the said monomer (C).

7. The composition of claim 6, wherein the said unsaturated carboxylic acid (A) is at least one member selected from the group consisting of acrylic acid, methacrylic acid, and undecenoic acid.

8. The composition of claim 6, wherein the said vinyl or allyl ester of an unsaturated carboxylic acid (B) is vinyl sorbate or allyl sorbate.

9. The composition of claim 7, wherein the said vinyl or allyl ester of an unsaturated carboxylic acid (B) is vinyl sorbate or allyl sorbate.

10. The composition of claim 6, wherein the said monomer (C) is a mono-functional (meth)acrylate-based monomer, a di-functional (meth)acrylate-based monomer, a tri-functional (meth)acrylate-based monomer, or a tetra-functional (meth)acrylate-based monomer.

11. The composition of claim 6, wherein the said setting agent is an oxidizing agent.

12. The composition of claim 6, wherein the said setting agent is an oxidizing agent/reducing agent combination, and wherein the said oxidizing agent and the said reducing agent are individually packed in at least two packages and are isolated from each other.

13. The composition of claim 6, wherein the said setting agent is an oxidizing agent/reducing agent combination in which the oxidizing agent is an organic peroxide and the said reducing agent is an amine, an amine salt, or an organic salt of sulfinic acid.

14. The composition of claim 12, wherein the said oxidizing agent is an organic peroxide, the said reducing agent is an amine, an amine salt, or an organic salt of sulfinic acid.

15. A dental adhesive resin composition, comprising:
(i) 0.5 to 10% by weight of at least one unsaturated carboxylic acid (A) of the formula:

$$R_1-CO-OH$$

where $R_1$ is a polymerizable hydrocarbon substituent having at least one double bond;

(ii) 0.5 to 20% by weight of at least one vinyl or allyl ester of an unsaturated carboxylic acid (B) having the formula:

$$R_1-CO-O-R_2$$

where $R_1$ is a polymerizable hydrocarbon substituent having at least one double bond, and $R_2$ is $CH_2=CH-$ or $CH_2=CH-CH_2-$; and (iii) a monomer (C) copolymerizable with the said unsaturated carboxylic acid (A) and the said vinyl or allyl ester of an unsaturated carboxylic acid (B);

(iv) said composition comprising from 0.1 to 10 parts by weight of a setting agent and up to 400 parts by weight of a filler, per 100 parts by weight of the said composition containing the said unsaturated carboxylic acid (A), the said vinyl or allyl ester of an unsaturated carboxylic acid (B) and the said monomer (C).

16. The composition of claim 15, wherein the said unsaturated carboxylic acid (A) is at least one member selected from the group consisting of acrylic acid, methacrylic acid, and undecenoic acid.

17. The composition of claim 15, wherein the said vinyl or allyl ester of an unsaturated carboxylic acid (B) is vinyl sorbate or allyl sorbate.

18. The composition of claim 16, wherein the said vinyl or allyl ester of an unsaturated carboxylic acid (B) is vinyl sorbate or allyl sorbate.

19. The composition of claim 15, wherein the said monomer (C) is a mono-functional (meth)acrylate-based monomer, a di-functional (meth)acrylate-based monomer, a tri-functional (meth)acrylate-based monomer, or a tetra-functional (meth)acrylate-based monomer.

20. The composition of claim 16, wherein the said monomer (C) is a mono-functional (meth)acrylate-based monomer, a di-functional (meth)acrylate-based monomer, a tri-functional (meth)acrylate-based monomer, or a tetra-functional (meth)acrylate-based monomer.

21. The composition of claim 17, wherein the said monomer (C) is a mono-functional (meth)acrylate-based monomer, a di-functional (meth)acrylate-based, a tri-functional (meth)acrylate-based monomer, or a tetra-functional (meth)acrylate-based monomer.

22. The composition of claim 18, wherein the said monomer (C) is a mono-functional (metha)acrylate-based polymer, a di-functional (meth)acrylate based-monomer, a tri-functional (meth)acrylate-based monomer, or a tetra-functional (meth)acrylate-based monomer.

23. The composition of claim 15, wherein the said setting agent is an oxidizing agent.

24. The composition of claim 15, wherein the setting agent is an oxidizing agent/reducing agent combination, wherein the said oxidizing agent and the said reducing agent are individually packed in at least two packages and are isolated from each other.

25. The composition of claim 15, wherein the said setting agent is an oxidizing agent/reducing agent combination in which the said oxidizing agent is an organic peroxide, and the said reducing agent is an amine, an amine salt, or an organic salt of sulfinic acid.

26. The composition of claim 24, in which the said oxidizing agent is an organic peroxide, and the said reducing agent is amine, an amine salt, or an organic salt of sulfinic acid.

27. The composition of claim 15, wherein the said filler is an organic filler, an organic fine powder, or a composite thereof.

28. The composition of claim 15, wherein the said filler is a MMA polymer.

29. A dental adhesive resin composition, comprising:
(i) 0.5 to 10% by weight of at least one unsaturated carboxylic acid (A) of the formula:

where $R_1$ is a polymerizable hydrocarbon substituent having at least one double bond;
(ii) 0.5 to 20% by weight of at least one vinyl or allyl ester of an unsaturated carboxylic acid (B) having the formula:

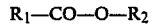

where $R_1$ is a polymerizable hydrocarbon substituent having at least one double bond, and $R_2$ is $CH_2=CH-$ or $CH_2=CH-CH_2-$; and
(iii) a monomer (C) copolymerizable with the said unsaturated carboxylic acid (A) and the said vinyl or allyl ester of an unsaturated carboxylic acid (B);
(iv) said composition comprising 0.1 to 10 parts by weight of a setting agent and 0.5 to 20 parts by weight of a silane compound, per 100 parts by weight of the said composition containing the said unsaturated carboxylic acid (A), the said vinyl or allyl ester of an unsaturated carboxylic acid (B) and the said monomer (C).

30. The composition of claim 29, wherein the said unsaturated carboxylic acid (A) is at least one member selected from the group consisting of acrylic acid, methacrylic acid, and undecenoic acid.

31. The composition of claim 29, wherein the said vinyl or allyl ester of an unsaturated carboxylic acid (B) is vinyl sorbate or allyl sorbate.

32. The composition of claim 29, wherein the said monomer (C) is a mono-tetra-functional (meth)acrylate-based monomer, a di-functional (meth)acrylate-based monomer, a tri-functional (meth)acrylate-based monomer or a tetra-functional (meth)acrylate-based monomer.

33. The composition of claim 29, wherein the setting agent is an oxidizing agent.

34. The composition of claim 29, wherein the setting agent is an oxidizing agent/reducing agent combination, wherein the said oxidizing agent and the said reducing agent are individually packed in at least two packages and are separated from each other.

35. The composition of claim 29, wherein the said setting agent is an oxidizing agent/reducing agent combination in which the said oxidizing agent is an organic peroxide, and the said reducing agent is an amine, an amine salt, or an organic salt of sulfinic acid.

36. The composition of claim 29, wherein the said silane compound is a compound of the formula:

wherein:
D is a hydrolyzable group;
n is an integer of 1 to 3;
b is 0, 1 or 2;
(n+b) is an integer of 1 to 3;
R' is a radical selected from the group consisting of monovalent hydrocarbons;
R is a $C_{1-4}$ alkylene group;
C is 0 or 1;
A is

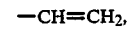

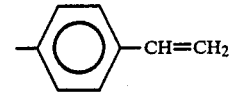

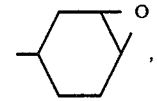

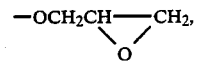

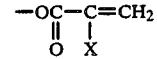

wherein X is a hydrogen atom or a $C_{1-6}$ hydrocarbon group.

37. A dental adhesive resin composition, comprising:
(i) 0.5 to 10% by weight of at least one unsaturated carboxylic acid (A) of the formula:

where $R_1$ is a polymerizable hydrocarbon substituent having at least one double bond;
(ii) 0.5 to 20% by weight of at least one vinyl or allyl ester of an unsaturated carboxylic acid (B) having the formula:

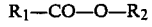

where $R_1$ is a polymerizable hydrocarbon substituent having at least one double bond, and $R_2$ is $CH_2=CH-$ or $CH_2=CH-CH_2-$; and
(iii) a monomer (C) copolymerizable with the said unsaturated carboxylic acid (A) and the said vinyl or allyl ester of an unsaturated carboxylic acid (B);
(iv) said composition comprising 0.1 to 10 parts by weight of a setting agent, up to 400 parts by weight of a filler, and from 0.5 to 20 parts by weight of a silane compound per 100 parts by weight of the said composition containing the said carboxylic acid (A), the said vinyl or allyl ester of an unsaturated carboxylic acid (B) and the said monomer (C).

38. The composition of claim 37, wherein the said unsaturated carboxylic acid is (A) is at least one member selected from the group of acrylic acid, methacrylic acid, and undecenoic acid.

39. The composition of claim 37, wherein the said vinyl or allyl ester of an unsaturated carboxylic acid (B) is vinyl sorbate or allyl sorbate.

40. The composition of claim 37, wherein the said monomer (C) is a mono-functional (meth)acrylate-based monomer, a di-functional (meth)acrylate-based monomer, a tri-functional (meth)acrylate-based monomer, or a tetra-functional (meth)acrylate-based monomer.

41. The composition of claim 37, wherein the said setting agent is an oxidizing agent.

42. The composition of claim 37, wherein the said setting agent is an oxidizing agent/reducing agent combination, wherein the oxidizing agent and the reducing agent are individually packed in at least two packages and are separated from each other.

43. The composition of claim 37, wherein the said setting agent is an oxidizing agent/reducing agent combination in which the said oxidizing agent is an organic peroxide, and said reducing agent is an amine, an amine salt, or an organic salt of sulfinic acid.

44. The composition of claim 37, wherein the said filler is an organic polymer, an inorganic fine powder, or a composite thereof.

45. The composition of claim 37, wherein the said filler is a MMA polymer.

46. The composition of claim 37, wherein the said silane compound is a compound of the formula:

wherein:
D is a hydrolyzable group;
n is an integer of 1 to 3;
b is 0, 1 or 2;
(n+b) is an integer of 1 to 3;
R' is a radical selected from the group consisting of monovalent hydrocarbons;
R is a $C_{1-4}$ alkylene group;
C is 0 or 1; A is $-CH=CH_2,$

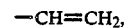

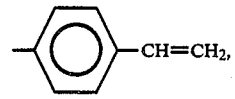

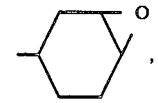

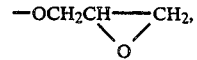

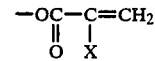

wherein X is a hydrogen atom or a $C_{1-6}$ hydrocarbon group.

* * * * *